United States Patent
Grimblatov (10) Patent No.: US 6,529,770 B1
(45) Date of Patent: Mar. 4, 2003

(54) METHOD AND APPARATUS FOR IMAGING CARDIOVASCULAR SURFACES THROUGH BLOOD

(76) Inventor: Valentin Grimblatov, 3000 Ocean Pkwy. #22L, Brooklyn, NY (US) 11235

(*) Notice: Subject to any disclaimer, the term of this patent is extended or adjusted under 35 U.S.C. 154(b) by 209 days.

(21) Appl. No.: 09/718,470

(22) Filed: Nov. 17, 2000

(51) Int. Cl.⁷ .............................. A61B 5/02; A61B 6/00
(52) U.S. Cl. ...................... 600/479; 600/473; 600/476; 600/478; 600/481; 600/500; 382/128; 382/130
(58) Field of Search .................................. 600/473, 476, 600/478, 481, 508, 479; 382/128, 130

(56) References Cited

U.S. PATENT DOCUMENTS

| | | | |
|---|---|---|---|
| 4,175,545 A | 11/1979 | Termanini | |
| 4,998,972 A | 3/1991 | Chin et al. | |
| 5,719,398 A | 2/1998 | Colak | |
| 5,799,656 A | 9/1998 | Alfano et al. | |
| 5,807,262 A | 9/1998 | Papaioannu | |
| 5,855,205 A | 1/1999 | Papaioannou | |
| 5,903,357 A | 5/1999 | Colak | |
| 5,941,827 A | 8/1999 | Papaioannou | |
| 6,023,341 A | 2/2000 | Colak | |
| 6,178,346 B1 * | 1/2001 | Amundson et al. | 348/77 |

FOREIGN PATENT DOCUMENTS

| | | |
|---|---|---|
| SU | 1208475 | 1/1986 |
| WO | WO 00/24310 | 5/2000 |

OTHER PUBLICATIONS

"Handbook or Photonics" M.C. Gupta.
"Spectroscopic Considerations", JJ. Burmeister et al, Infrared Spectroscopy 04–98.
"Optomechanical effect of tissue blood microcirculation under compreshion", V. Grimblatov, Columbia Pres Gyterian Medical Care "Diagnostics of Leus Like Biological media", V. Grimblatov et al.

* cited by examiner

Primary Examiner—Marvin M. Lateef
Assistant Examiner—Jeoyuh Lin
(74) Attorney, Agent, or Firm—I. Zborovsky (57) ABSTRACT

A technique for imaging cardiovascular surfaces through blood using a combination of spectral and spatial selection of radiation being reflected diffused back and by a blood vessel interior. Imaging a cardiovascular surface includes intralumenal irradiating a cardiovascular interior through blood with a radiation of a wavelength with minimum of total optical losses through blood, so that the radiation of the wavelength is reflected and backscattered at least partly by a cardiovascular surface, detecting all intensity signals of the reflected and backscattered radiation, and processing the detected signals by selecting intensity signals of radiation being backscattered by blood only, and subtracting the selected intensity signals of radiation backscattered only by blood from all detected intensity signals of reflected and backscattered radiation, so as to reconstruct an image of the cardiovascular surface using the intensity signals of difference obtained by subtracting. Differential processing the intensity signals of radiation diffused back only by blood enable extreme improvement of the contrast of an image signal at maximal viewing distance.

25 Claims, 10 Drawing Sheets

METHOD AND APPARATUS FOR IMAGING CARDIOVASCULAR SURFACES THROUGH BLOOD

FIELD OF THE INVENTION

The invention relates generally to the imaging of body passage surfaces through body fluids and, in particular, to a novel technique for imaging cardiovascular surfaces through blood. The invention also relates to an apparatus for carrying out a method of such kind. Such method and apparatus can be advantageously used in examination of cardiovascular surfaces and conducting minimally invasive procedures in cardiovascular surgery.

BACKGROUND OF THE INVENTION

Direct visualization of body passages has become a routine procedure now. Modern endoscopic technique is used for viewing and imaging different body passages, such as gastrointestinal tract, bronchial passages, joints, cardiovascular system. Most of the passages are filled with body fluids, such as blood, urine, stomathic fluids which are opaque for illumination and prevent visualization of the passage's surfaces. For passages not filled with blood it is not a problem because in such body cavities as stomach or esophagus the fluid can be evacuated to clear the visualization field. Similar technique is used in angioscopy. Sterile saline flush solution is introduced into the vessel continuously or periodically for blood evacuation (U.S. Pat. No. 4,998,972 issued Mar. 3, 1991 to Chin Albert K. et. al,; U.S. Pat. No. 4,175,545 issued November 1979 to Termanini). Such procedure provides user with very short time of vision determined by the length of irrigation period. It is particularly difficult to perform this procedure in arterial system where pressure and flow rate of blood are much higher than in veins. It makes difficult to obtain enough clear bloodless field for visualization of the cardiovascular surfaces.

Ability to see through blood would enable revolutionary new approaches in diagnosis and treatment of cardiac, arterial, and venous diseases.

In standard angioscopy procedure a light delivered into a lumen of a cardiovascular passage irradiates the interior. Only backscattered and reflected light is available for imaging. Radiation being reflected and scattered by the surface structure at least partly is detected and intensity signals are used to produce image signals. High concentration of blood cells along with discontinuing in the index of refraction at the interface between plasma and cells make blood a multiply scattering and absorbing medium. Thus, imaging through blood is imaging of diffused and reflected by the surface structure light being scattered many times before it reaches the detector. Because of that the radiation detected at any location of back-scattered flux contains a contribution of scattering from all regions of the irradiated interior resulting in a strong background presence in the detected signals. The background masks the actual intensity signals containing imaging information about the cardiovascular surface. Along with decreasing the contrast of an image signal the scattering attenuates signal itself and limits the optical path length (OPL) in blood. One of the most difficult aspects of imaging through blood is to obtain maximal image signal contrast at maximal optical path length.

With taking into account that only the radiation collected within a field of view of the acquiring optical system is detected and that the angle of view of the cardiovascular surface, $\phi$, is different from the angle of view of the interior, $\varphi$, the detected part of incident radiation $I_0$ is described by equation $$I = I_0 [\tau^2 \rho_s \phi_s + \rho_b \phi] \quad (1)$$

where $\tau$ is the blood transmittance at the wavelength of irradiation and $\rho_s$ is the surface reflectance, $\rho_b$ is the blood diffuse reflectance.

For intraluminal irradiation, the blood can be considered as a semi-infinite medium and the term "diffuse reflectance" characterizes the light emergent the semi-infinite medium back to irradiating side due to scattering. The transmittance and diffusive reflectance in eq. (1) are determined by blood optical properties characterized by an absorption coefficient, $\mu_a$ and reduced scattering coefficient (coefficient of scattering back), $\mu'_s$ per unit length. In diffusion approximation of a semi-infinite cardiovascular interior the radiation backscattered by blood can be characterized by a diffuse reflection [S. Jacques, Diffuse reflectance from a semiinfinite medium. OMC & Report, May 1998] and approximated by expression:

$$\rho_d^\infty = exp(-A/\sqrt{3(1+N)})$$

and the equation (1) can be re-written in form:

$$I = I_0 \left[ \rho_s \varphi_s exp(-2\sqrt{3\mu_a \mu_t}\, l) + \varphi exp\left(\frac{-A}{\sqrt{3(1+N')}}\right) \right] \quad (2)$$

with a total attenuation coefficient $\mu_t = \mu_a + \mu'_s$ and diffuse reflectance characterizing parameter $$N' = \frac{\mu'_s}{\mu_a}$$

Here l is the optical path length, and the factor $$A = -\ln\left(\frac{I}{I_0}\right)$$

The value of A depends on reflectance parameter N' and refractive index mismatch at the blood-air interface. As it is seen from eq. (2), the primary component of the detected intensity signals is a strong background not containing information about the vessel surface. Such strong background extremely decreases contrast of the intensity signals and dramatically shortens the viewing distance through blood. Once the radiation being diffused back by blood (the second term in eq. (2)) and reflected by the vessel surface (the first term in eq. (2)) are specified, one can calculate the contrast of the intensity signal:

$$K = \frac{\rho_d}{\rho_s} = exp\left[-\frac{A - 3\mu_t l}{\sqrt{3\mu_t \mu_a}}\right]$$

Figure 1:
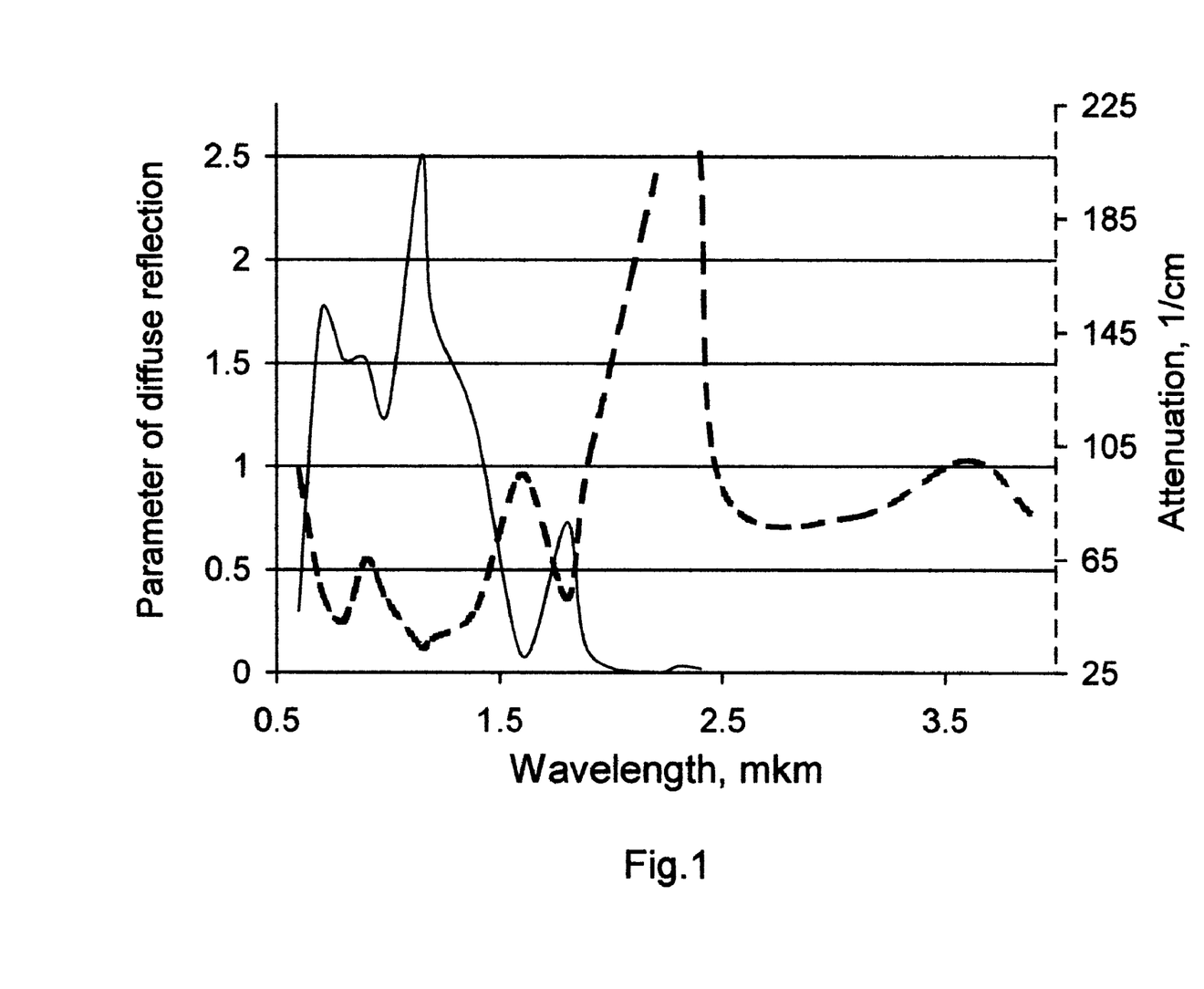
FIG. 1 represents optical spectra of the parameters of total attenuation in and diffuse reflection from blood

Optical properties of blood are dependent on wavelength and, therefore, total attenuation and diffuse reflection are also wavelength depend. As a result the intensity signal and its contrast strongly vary with wavelength. That makes attractive to enhance the intensity signal and improve the contrast at the same time simply by selecting an "optimal" wavelength. International patent application WO 00/24310 published in May 2000 discloses a device and method for imaging through body fluids simply by using the radiation of mid Infrared (IR) spectrum regions (1.4 to 1.8 mkm, 2.1 to 2.4 mkm, 3.7 to 4.3 mkm, 4.6 to 5.4 mkm, and 7 to 14 mkm). Blood has obviously reduced scattering in mid IR region. As per inventors' statement the absorption is also extremely low at mid IR wavelengths because water as the main part of blood has optical windows at these wavelengths. However, modern experimental data shows that radiation of above mentioned wavelengths is strongly absorbed by blood glucose [Jason J. Bumeister and Mark A. Arnold *Spectroscopic considerations for noninvasive blood glucose measurements with near infrared spectroscopy,* Infrared Spectroscopy, p. 2, 1999] and other blood components [A. Roggan et. al. *Optical properties of circulating blood in the wavelength range* 400–2500 *nm,* J. of Biomedical Optics, Vol. 4, pp. 36–46, 1999] resulting in an unacceptably short OPL. Total attenuation and diffuse reflectance spectra derived from published data are shown in FIG. 1. It is seen that total attenuation in and diffuse reflectance from blood have different spectra and at the wavelength of the signal contrast improvement (mid IR) the total attenuation is unacceptably high.

Numerous techniques for optical imaging based on special processing the detected signals are known in the art. Most of them use a transmission mode imaging. The term "transmission mode" is regarded to detecting the radiation passed through the turbid medium. Methods of this kind are known from the article B. Chance et. al. *Highly sensitive object location in tissul models with linear m. phase and anti-phase multielement optical arrays in one and 2 dimersoons,* Proc. of the National Academy of Science USA, Vol. 90 (1993) 3423–3427 and U.S. Pat. No. 5,807, 262 issed Sep. 15, 1998 to Papaioannou Dimitoios. By transilluminating the turbid medium with a set of couples of beams being modulated in anti-phase the contribution of scattering to the background signals is reduced and under certain conditions the background even can be cancelled. If an object that typically absorbs the radiation is present in the medium the detected signals at the frequency of modulation becomes different from predetermined. Such technique is suitable for imaging only absorbing objects embedded in a turbid medium with wavelength independent absorbance, which obviously is not the blood. Besides that, the requirement to use a plurality of irradiating beams is not applicable for cardiovascular lumen sizes.

Various principles of reconstructing an image of a turbid medium interior by determining differences between measured and theoretically predetermined values of different parameters of passed through the turbid medium radiation are disclosed in U.S. Pat. No. 5,903,357 to Colak Sel B. issued May 11, 1999; U.S. Pat. No. 5,719,398 to Colak Sel B. issued Feb. 17, 1998 and U.S. Pat. No. 6,064,073 to Hoogenraad Johannes issued Jul. 14, 1998. Such parameters are the attenuation coefficient of a voxel of the turbid medium, intensity of light entering the turbid medium from different directions, convolution function of light transported through turbid medium. Not discussing the boundaries of applicability of used theoretical models just note that all of them consider only a large-scale homogeneous medium with spectral independent absorption. Unfortunately, the blood is a turbid medium containing large and small-scale inhomogeneities with the absorption being strongly dependent on wavelength especially in visible and near infrared spectrum [Valentin Grimblatov and A. Bekshaev, *Diagnosis of lens-like biological media,* Proc. SPIE, Vol. 2626, pp. 24–32, 1995] for which such technique is not applicable.

Transillumination of the turbid medium along with adjusting optical properties and measuring differences between intensity of passed through the medium radiation before and after adjustment is disclosed in U.S. Pat. No. 6,023,341 to Coiak Sel B. issued Feb. 8, 2000. Having all above described disadvantages this method of adjusting the medium optical properties by compression is principally not applicable to blood. As it has been shown in the article Valentin Grimblatov and Alexander Bekshaev, *Optomechanical effect of tissue blood microcirculation under compression,* Proc. SPIE, Vol. 3253, 1999 even light compression of the blood volume in cardiovascular passage brings to a non-linear changes in optical properties of blood. Besides that, in the visible spectrum that is used in this method both the total attenuation and diffuse reflection are extremely high.

A method and system of irradiating the turbid medium with anti-phase modulated dual wavelength radiation of visible spectrum (0.6 mkm–1 mkm) is disclosed in U.S. Pat. No. 5,941,827 to Papaioannon Dimitrous issued Aug. 24, 1999. Such technique can increase the image signal contrast but is suitable for viewing only absorbing objects embedded in a turbid medium with wavelength independent absorbance which obviously cannot be blood.

An alternative technique of imaging objects in turbid medium is temporal and special gating the radiation emergent from the turbid medium based on time resolved spectroscopy [U.S. Pat. No. 5,625,458 to Alfano R. R. and Polishchuk Alexander Y. issued Apr. 29, 1997, U.S. Pat. No. 5,799,656 to Alfano R. R. et al issued Sep. 1, 1998] and heterodyne processing the signals [U.S. Pat. No. 5,855,205 to Papaioannon Dimitrous and Hoolfgerf W. issued Jan. 5, 1999]. Such technique extremely increases the contrast but always shortens the viewing length.

Thus, the known techniques of optical imaging are unable for imaging cardiovascular surfaces through blood. No art has been found for technique of maximizing the viewing length along with improving the contrast of the image signal in "reflectance mode" where defecting is produced at the same side of the turbid medium as irradiating.

SUMMARY OF THE INVENTION

An object of the present invention is to provide a technique for imaging a body passage surface through the body fluids, which is free from above described disadvantages. More particularly an object of the invention is to provide a method and apparatus for imaging cardiovascular surfaces through blood capable of providing maximal viewing distance along with increased contrast of the image signals.

In keeping with these objects and with others which will become apparent hereinafter, one feature of present invention resides, briefly stated, in a method of imaging cardiovascular surfaces through blood, comprising the steps of intralumenally irradiating a cardiovascular interior through blood with a radiation of a first wavelength with minimum of total optical losses through blood, so that that the radiation of a first wavelength is reflected and backscattered at least partly by a cardiovascular surface, detecting all intensity signals of reflected and backscattered radiation, and processing the detected intensity signals by selecting intensity signals of radiation being backscattered by blood only, and subtracting the selected intensity signals of radiation backscattered only by blood, so as to reconstruct an image of the cardiovascular surface using the intensity signals of difference obtained by said subtracting.

In accordance with another feature of present invention, an apparatus for imaging cardiovascular surfaces through blood is provided, which includes means for intralumenally irradiating a cardiovascular interior through blood wit radiation of a first wavelength with minimum of total optical losses through blood, so that the radiation of a first wavelength is reflected and backscattered at least partly by a cardiovascular surface; means for detecting all intensity signals of reflected and backscattered radiation; and means for processing the detected intensity signals by selecting intensity signals of radiation beackscattered by blood only and subtracting the selected intensity signals of radiation backscattered only by blood from the all detected intensity signals of reflected and backscattered radiation, so as to reconstruct an image of the cardiovascular surface using the intensity signals of difference obtained by said subtracting.

For imaging through blood, a combination of spectral and spatial selection is discovered to permit maximization of the viewing length through blood and extreme increase of the signal contrast.

It will be seen that absorption and scattering of the turbid medium produce fundamentally different effect on the image signal. While absorption just attenuates radiation propagating in a turbid medium the scattering produces a dual effect. Along with contributing in signal attenuation the multiple scattering results in a strong background presence in the image signal. Accordingly, the intensity signals being used for imaging through a turbid medium, such as blood, are weak and have a dramatically low contrast. Conventional imaging technique of seeing through a turbid medium employs spectral selection of ranges in visible and mid IR and various methods of processing the intensity signals being able to increase at special conditions either the viewing length or the contrast of the intensity signals. However, none of them is applicable to see through blood and increase contrast of corresponding intensity signals at the same time.

This patent application discloses a technique of imaging the cardiovascular surface through blood by using spectral selection of radiation of a wavelength corresponding to the maximal optical path length (OPL) in blood combined with selection of radiation diffused back only by blood and differential processing of the signals. The term "differential processing" in the instant invention refers a process of producing a signal of difference between intensity signals corresponding to radiation being diffused back only by blood and by the whole vessel interior. Despite describing in this application the method and apparatus for imaging cardiovascular surfaces through blood, they are applicable for imaging the surface of any body passage through an opaque and turbid medium. Blood is considered throughout this application just as the most important body fluid.

The fundamental teaching in this patent is that scattering produces a dual effect on the intensity signals. The length of view in blood is limited by attenuation of the radiation due to absorption and scattering and a strong background presence in the intensity signal. As disclosed below there exist a spectral region in near IR where the total optical losses through blood are absolutely minimal. A principal teaching is that the line of the maximal OPL in blood classifies areas of an image zone onto those corresponding to radiation diffused back only by blood and being reflected and scattered by whole interior. The differential processing of the intensity signals of classified areas extremely increases the contrast of the signals corresponding to maximal length of view. Selection of the radiation being diffused back only by blood is based on a predetermined locating the corresponding area of the image zone.

A second principal teaching is that radiation attenuation through and diffuse reflection from blood have different optical spectra. As disclosed below a dramatically increased contrast of the image signals at maximum length of view is achieved by intraluminal irradiation of the cardiovascular interior with radiation of two wavelength one of which corresponds to maximum OPL and the other wavelength corresponds to the OPL being less than the lumen size. Having the total attenuation at the second wavelength strong enough to prevent the radiation from reaching the cardiovascular surface the background is eliminated by subtracting the intensity signals of second wavelength from those of the first wavelength.

The disclosed technique is accomplished by disclosing an apparatus utilizing above method and able for imaging cardiovascular surfaces through blood at maximum length of view with extremely improved contrast of the image signals.

A transparent to blood imaging technique has revolutionary consequences in diagnosis and treatment inside the heart or in the vasculature. Besides cardiology the disclosed imaging through blood technique would benefit several other medical disciplines, such as oncology, neurology etc.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

The accompanying drawings are part of the specification and illustrate various embodiments of the invention. They serve also to explain the principles of the invention.

DESCRIPTION OF THE PREFERRED EMBODIMENTS

Figure 2:
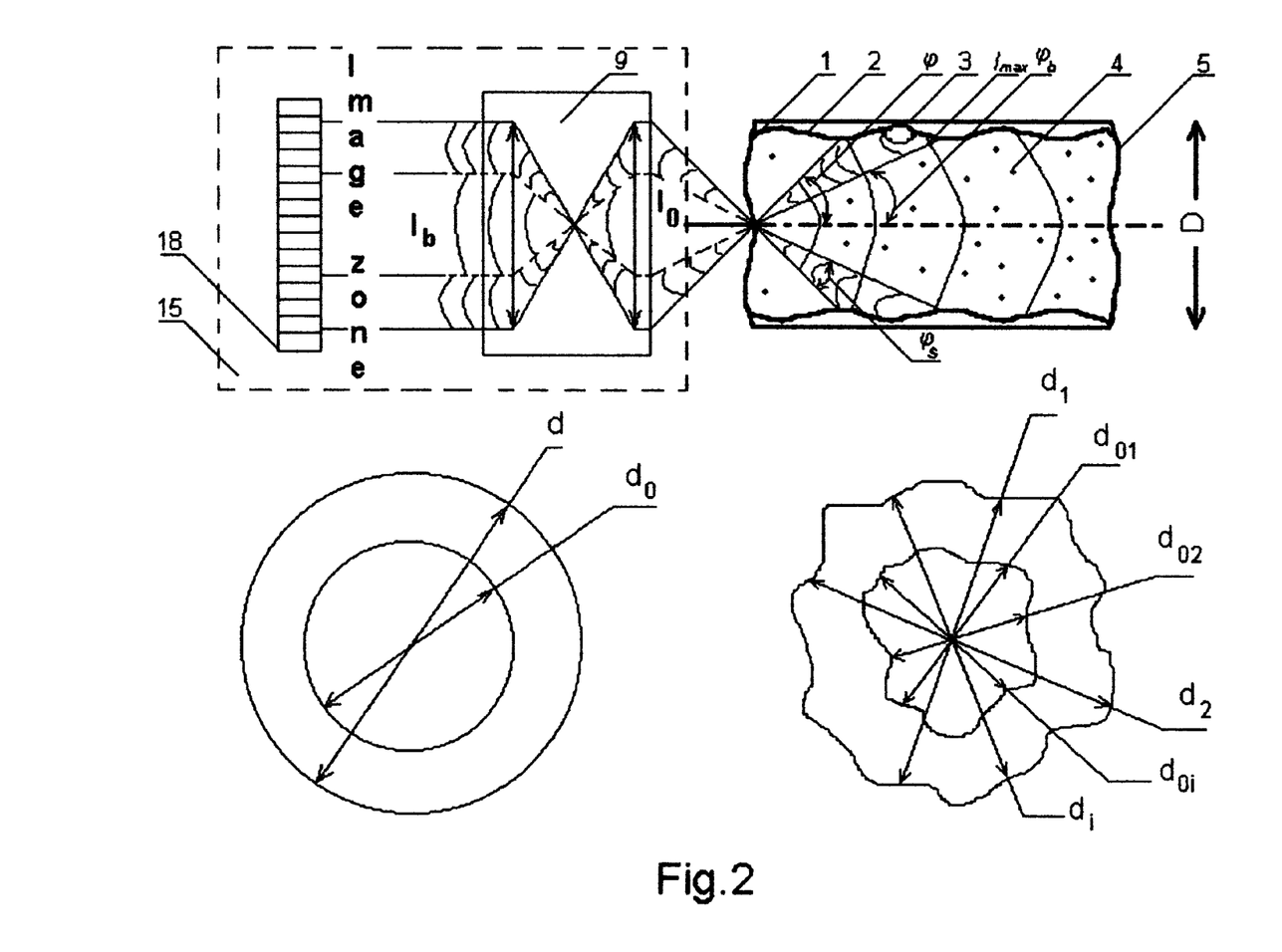
FIG. 2 is a graphic representation of parameters being used for explanation of the principles of the invention

As indicated above, the present invention is based upon the present inventor's discovery that radiation being diffused back only by blood is identified by locating areas of an image zone being classified by the line of maximal OPL. FIG. 2 shows basic parameters that are employed in classifying the radiation diffused back by the blood and reflected by the vessel surface. Delivered into the blood vessel radiation $I_0$ is reflected and diffused back by the vessel interior. The diffused back and reflected radiation I is collected within a collection field of view $\phi$ and transformed into an image zone radiation by an acquiring optics 9. The central area of the image zone corresponds to radiation being diffused back by blood only. This area is conveyed by circumference determined by a line of the maximal OPL in blood and the vessel surface. From simple geometrical considerations (see FIG. 2) the diameter of this area is determined by expression $$d_0 = \frac{\left(2f\sqrt{l_{max}^2 - \frac{D^2}{4}}\right)}{l_{max}} \quad (3)$$

and intensity signal of corresponding radiation is $$I = I_0\varphi_0 \exp\left(\frac{-A}{\sqrt{3(1+N')}}\right) \quad (4)$$

When the area has a form of broken line the diameter is a set of local diameters (see FIG. 2). Multiple scattering permits radial averaging the intensity signals of radiation over this area. The subtraction of the averaged intensity signal from the intensity signals of radiation of the annulus results in signals of difference with markedly reduced background:

$$I - I_b = I_0\left[\varphi_s \exp\left(-2\sqrt{3\mu_a\mu_t}\, l\right) + \varphi_b\left(1 - \frac{\varphi}{\varphi_b}\right)\exp\left(\frac{-A}{\sqrt{3(1+N')}}\right)\right] \quad (5)$$

The ratio $$\frac{\varphi}{\varphi_b}$$

is made equal to 1 simply by adjusting the amplitude of the average intensity signal, and $$I - I_b = I_0\varphi_s \exp(-2\sqrt{3\mu_a\mu_t}\, l) \quad (6)$$

Here $\varphi_s$ is a field of view the vessel surface.

The maximal distance of view is achieved by using radiation of the wavelength corresponding to absolute minimum of total optical losses through blood. Such wavelengths are preferably from about 1 mkm to about 1.2 mkm (FIG. 1). For example, the absorption and back-scattering coefficients derived from published data are 4 cm$^{-1}$ and 27 cm$^{-1}$, correspondingly. The total attenuation of radiation at distance 1 cm is $$exp(-\sqrt{3\cdot 4\cdot 32}) = 3\cdot 10^{-9}$$

Conventional IR cameras detect radiation of power about ln W or $$10^{-9}\ W$$

Therefore, an incident radiation of power about 3W is enough to see through blood at distance 1 cm. Such power is below the threshold of blood damage and is quite acceptable for diagnostics. To see through blood at the same distance at wavelength 0.8 mkm the power about 22,000W is required, which is absolutely unacceptable for diagnostic purposes.

Figure 3:
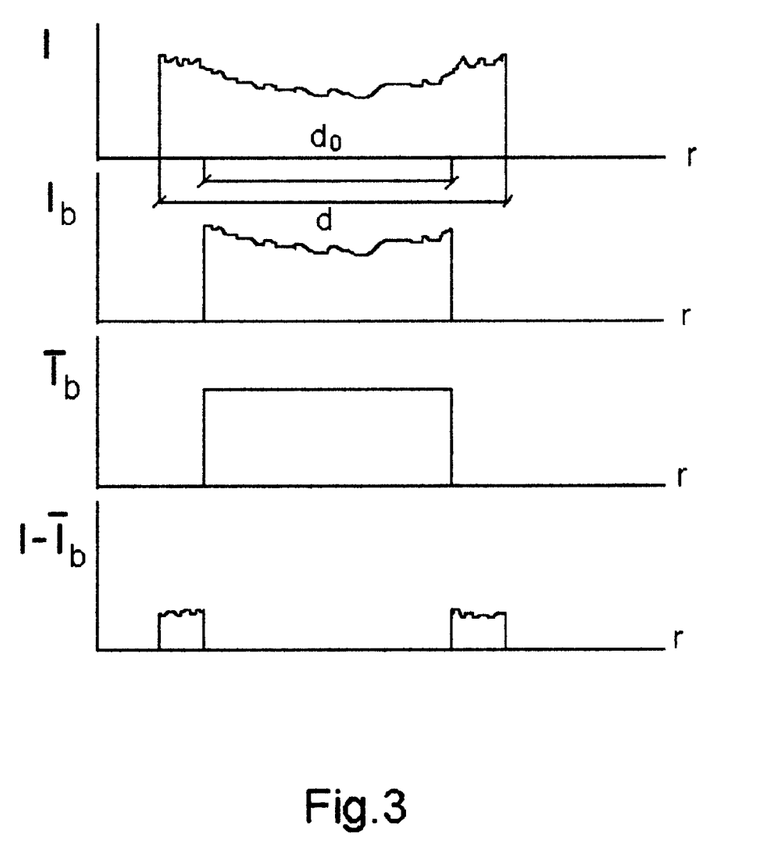
FIG. 3 is an illustration of the intensity signal transformation according to a preferred embodiment

Obtained signals of difference are used as image signals for reconstructing an image of the vessel surface. Corresponding transformations of the intensity signals are shown in FIG. 3.

Figure 4A:
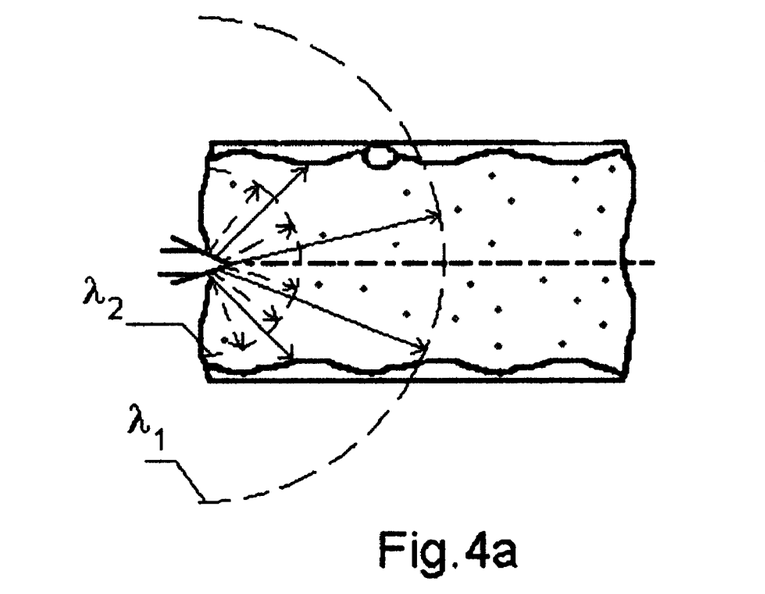
FIG. 4 is a schematic representation of the intralumenal irradiation of a blood vessel
Figure 4B:
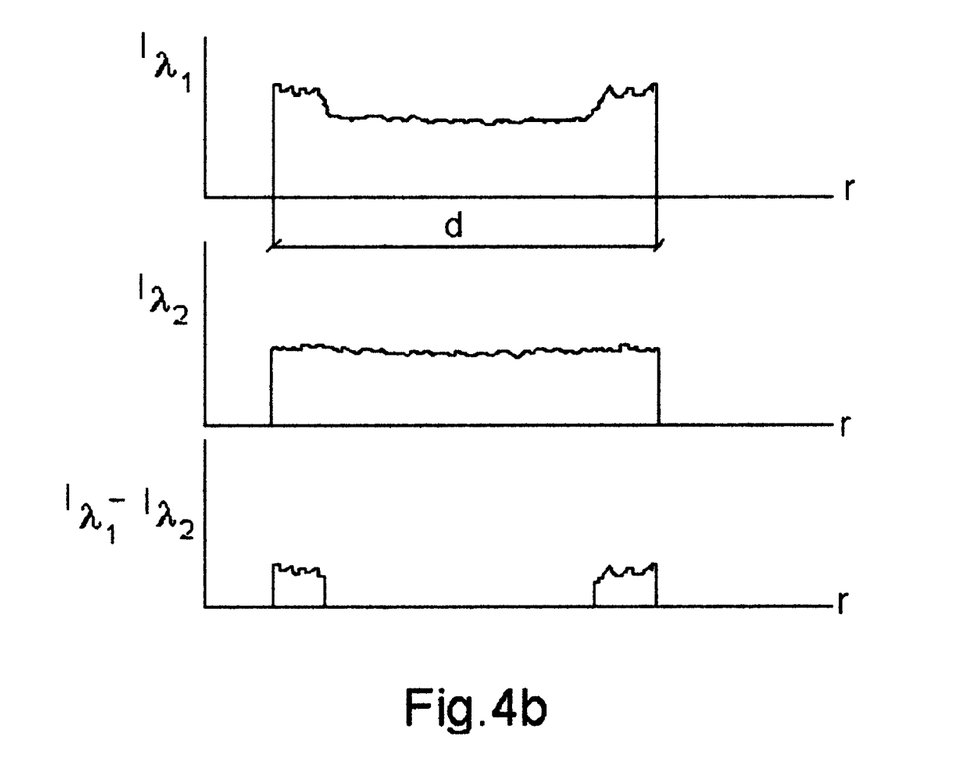

A next version of a method according to the invention is characterized in that the vessel interior is irradiated with dual wavelength radiation having a first wavelength corresponding to absolute minimum of total optical losses through blood and a second wavelength corresponding to an optical path length in blood being less than the vessel lumen size (FIG. 4a). The intensity signals of radiation of the first and the second wavelength are obtained similarly to the equation (1):

$$I_{\lambda 1} = I_{01}[\tau_1^2 R_s \phi_s + \rho_{1b}\phi] \quad (7)$$

$$I_{\lambda 2} = I_{02}[\tau_2^2 R_s \phi_s + \rho_{2b}\phi] \quad (8)$$

Here $\rho_{1b}$ and $\rho_{2b}$ are the diffuse reflectance coefficients at the first and second wavelength correspondingly.

Selection of the second wavelength corresponding to the OPL being less than the vessel lumen size opaque the surface and deletes the first term in equation (8). Further subtraction of the intensity signals of the second wavelength radiation from the signals of the first wavelength radiation reduces the contribution of the blood diffusion back and extremely improves the contrast of the image signal $$I_{\lambda 1} - I_{\lambda 2} = I_0[\tau_1^2 R_s \phi_s + (\rho_{1b} - \rho_{2b})\phi]$$

Adjustment of the intensity of the second wavelength radiation makes $\rho_{1b} = \rho_{2b}$ and accomplishes elimination of the background $$I_{\lambda 1} - I_{\lambda 2} = I_{01}\tau^2 R_s \phi_s \quad (9)$$

To keep $\tau_1 = \tau_2$ the second wavelength shall be adjacent to the first one and be preferably from about 0.8 mkm to about 1 mkm or from about 1.2 mkm to about 1.4 mkm.

Figure 5:
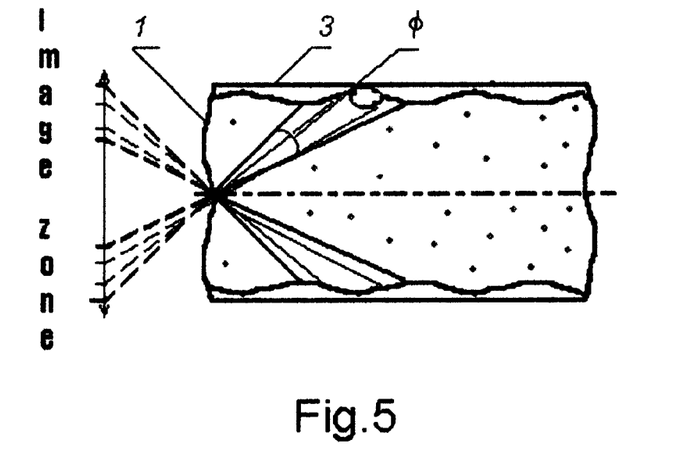
FIG. 5 is an illustration of the image signal forming

Another version of a method according to the invention is illustrated in FIG. 5. Irradiation of the vessel interior is provided within a ring shaped cone. The intensity signals of detected radiation contain both contributions of radiation being diffused back by blood and reflected by the vessel surface within the same collection field of view $\phi_s$. That allows eliminating the background from image signals simply by subtraction the intensity signals of the second wavelength from those of the first wavelength. Such radiation delivery pattern and collection field of view are achieved by a specially designed fiber with reflective coating or incapsulants as it is described in U.S. Pat. No. 5,953,477 to Michael Wach and Eric Marple issued Sep. 14, 1999.

Figure 6:
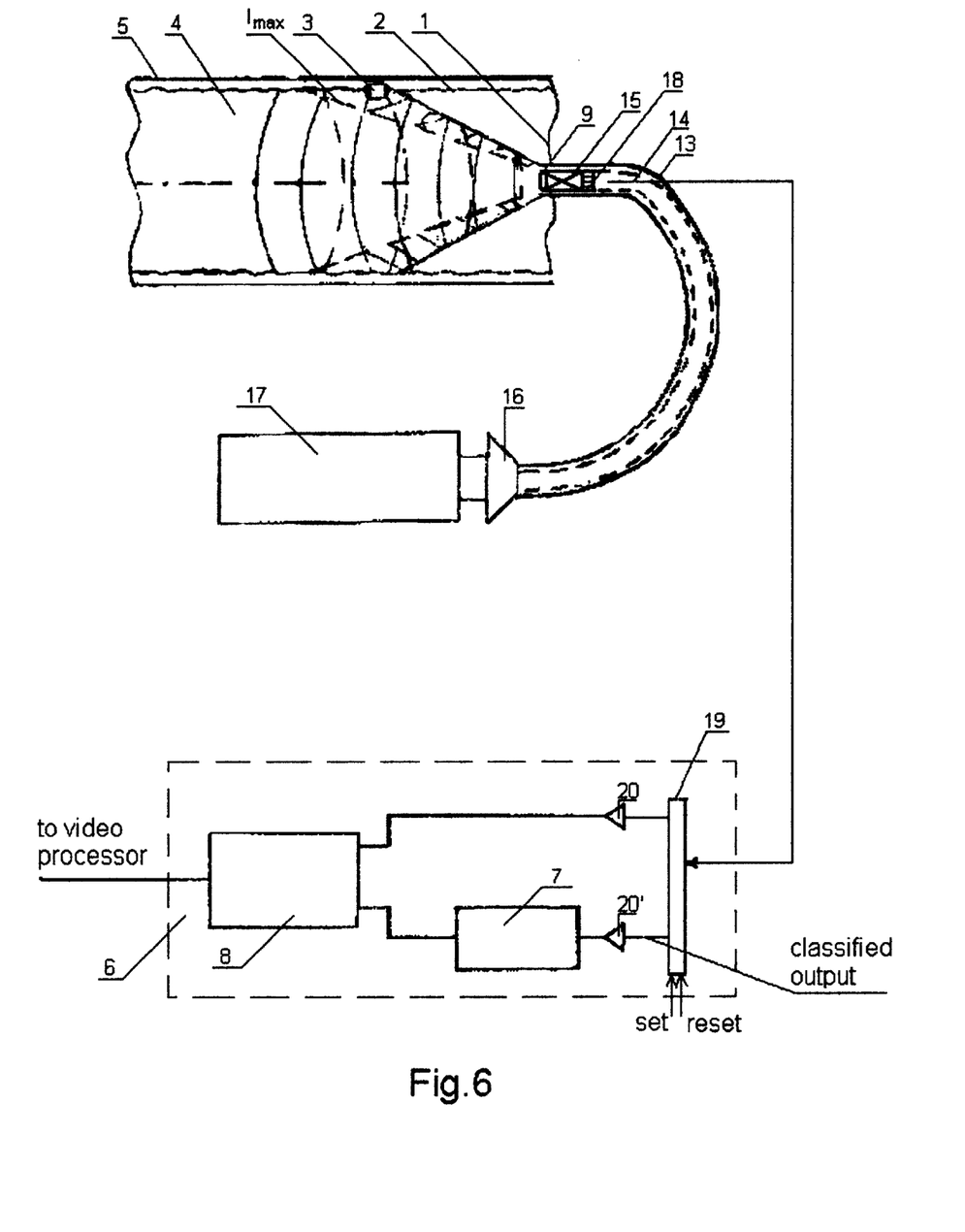
FIG. 6 is a schematic representation of an apparatus according to a preferred embodiment

A further object of the invention is to provide an apparatus for imaging cardiovascular surfaces through blood. FIG. 6 schematically shows an apparatus for imaging surfaces of a blood vessel, such as vein or an arteria, in accordance with the general concept of present invention. The scope 13 having the proximal and the distal ends contains a transmission channel 14 for transporting radiation from a source 17 of radiation of a first wavelength into the lumen 1 of a blood vessel 5 and an acquisition channel 15 for detecting the radiation being reflected from the vessel interior. A standard rigid scope suitable to the vessel lumen size, such as Karl Storz model 1101RD, can be used. A fiber optic coupler 16 matches parameters of the source beam and proximal end of the acquisition channel. Radiation of the first wavelength is delivered into the lumen and emergent the distal end of the acquisition channel within a cone of irradiation as is shown in FIG. 2. The reflected and diffused back radiation is collected within a collection field of view $\phi$ by an acquiring optics 9 that is arranged at the distal end of the acquisition channel and further transformed into an image zone radiation (FIG. 2). The image zone radiation is detected by a photodetector 18 which is in fact a CCD-sensor being electrically connected to a signal processor 6. The radiation acquired within the collection field of view contains contributions of diffused back by blood and reflected by the vessel surface radiation. As it is illustrated in FIG. 2, the diffused back by blood radiation is collected within a field of view $\phi_b$ determined by a cone angle being formed by a line of maximal OPL and vessel surface. Radiation of region from about 1 mkm to about 1.2 mkm is preferable because in this range the blood has absolutely minimal total optical losses (see FIG. 1). The field of view $\phi_b$ corresponds to a central area of the image zone (FIG. 2). The CCD sensor 18 converts radiation of the image zone into electrical intensity signals which further are fed to the signal processor 6 comprising a read-out-circuit 19 and a first and second signal amplifiers 20 and 20', accordingly, and a signal averaging unit 17 and a signal subtractor 8. The intensity signals from the CCD sensor are read out by a programmable read-out-circuit 19 to the first and second amplifiers. Accordingly to predetermined settings the intensity signals of the central area of the image zone containing only blood diffused back radiation are read out to the second amplifier and then are averaged by the signal averaging unit 17. The outputs of the first amplifier and the signal averaging unit 17 are electrically connected to the signal subtractor 8, which produces signals of difference not containing background. A standard digital DC offset amplifier described in *Design of Pulse Oximeters,* edited by J. G. Webster, pp. 107–109, Bristol and Philadelphia, 1997 or an electronic signal subtractor disclosed by V. Grimblatov in U.S. patent application Ser. No. 09/178,788 is used. The image signals further are converted by a video processor into video signals being supplied to a monitor. The source of radiation is a laser or a Light Emitted Diode (LED).

Figure 7A:
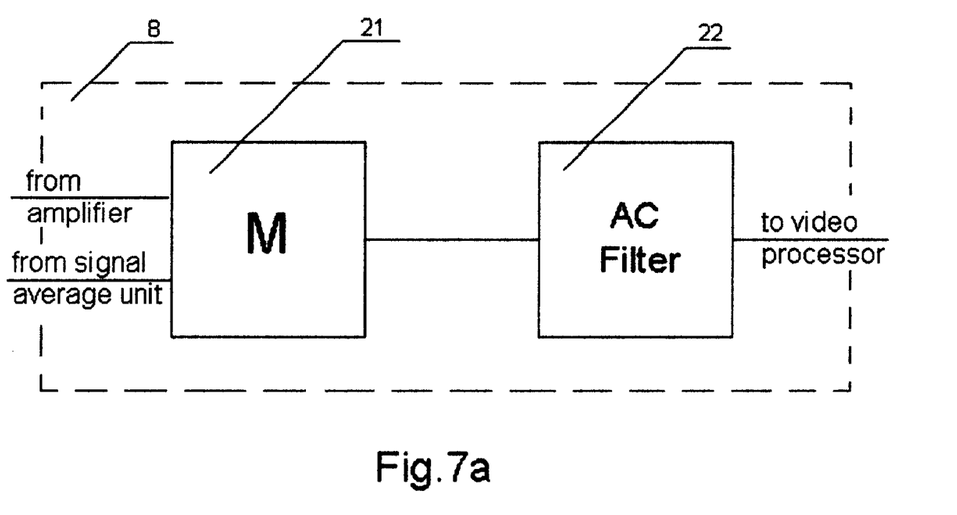
FIG. 7 is a block-diagram of a signal subtractor according to a preferred embodiment

In a further preferred embodiment illustrated in FIG. 7a the signal subtractor 8 comprises a modulator 21 for anti-phase amplitude modulation of the intensity signals from the signal averaging unit 7 and the first amplifier and an A.C. filter 22 tuned to the frequency of modulation for selecting the A.C. component of the intensity signals. Anti-phase modulation means supplying the average intensity signal while blocking the intensity signals of annulus and visa versa. Within central area of the image zone the intensity signals have about the same amplitude and anti-phase modulation does not produce an A.C. component at the frequency of modulation. Outside the classified area the signals have different amplitude and an A.C. component with amplitude dependent on the differences between intensity signals is occurred:

$$I_{A.C.} = I_0 \varphi_s \left[ \exp(-2\sqrt{3\mu_a \mu_t} \, l_{max}) + \left(1 - \frac{\varphi_b}{\varphi_s}\right) \right] \quad (10)$$

Amplification of the classified area intensity signals results in $$\frac{\varphi_b}{\varphi_s} = 1$$

and accomplishes the contrast improvement $$I_{A.C.} = I_0 \varphi_s \exp(-2\sqrt{3\mu_a \mu_2 l_{max}}) \quad (11)$$

Figure 7B:
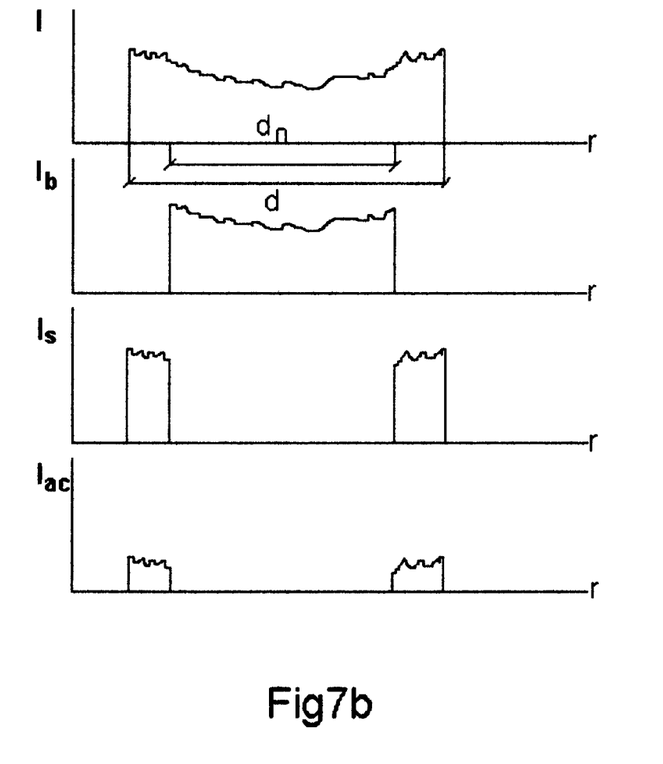

Corresponding signal transformations are shown in FIG. 7b.

Figure 8:
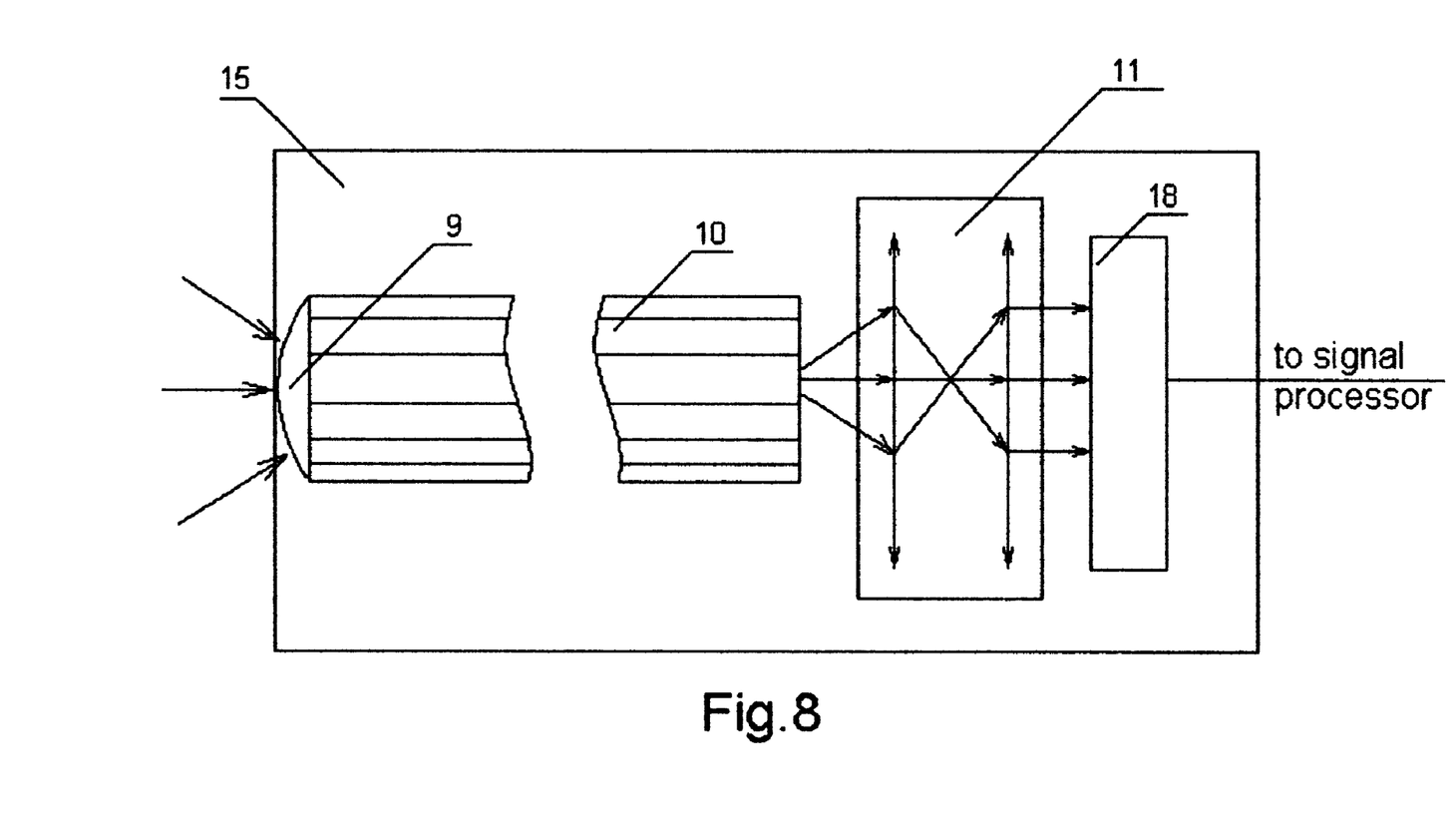
FIG. 8 is a block-diagram of an acquisition channel according to a preferred embodiment

In another preferred embodiment according the invention shown in FIG. 8 the acquisition channel of the apparatus further comprises a fiber optic cable 10 engaged with the acquiring optics 9 for transmitting the collected radiation to an image optics 11 arranged in front of the CCD sensor 18 for forming the image zone radiation.

Figure 9A:
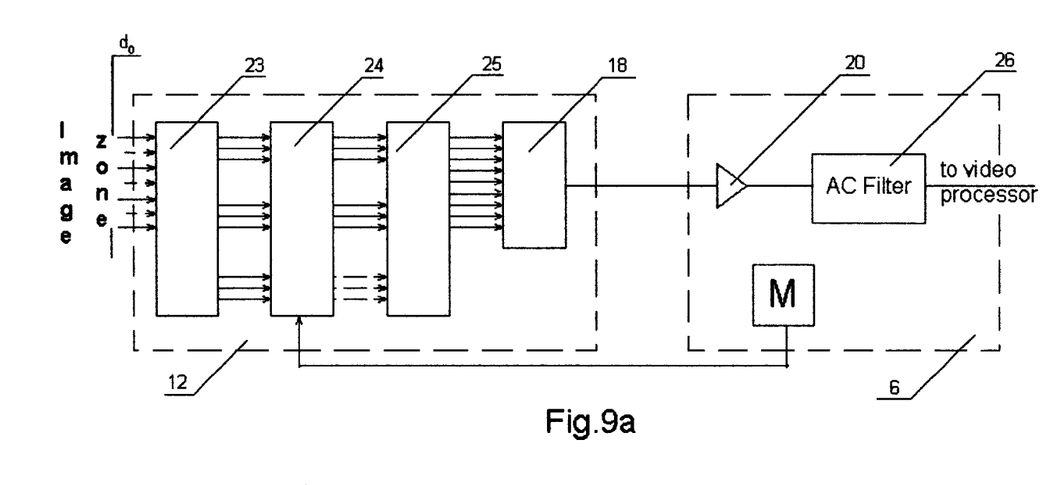
FIG. 9 is a block-diagram of an optical alternator according to a preferred embodiment
Figure 9B:
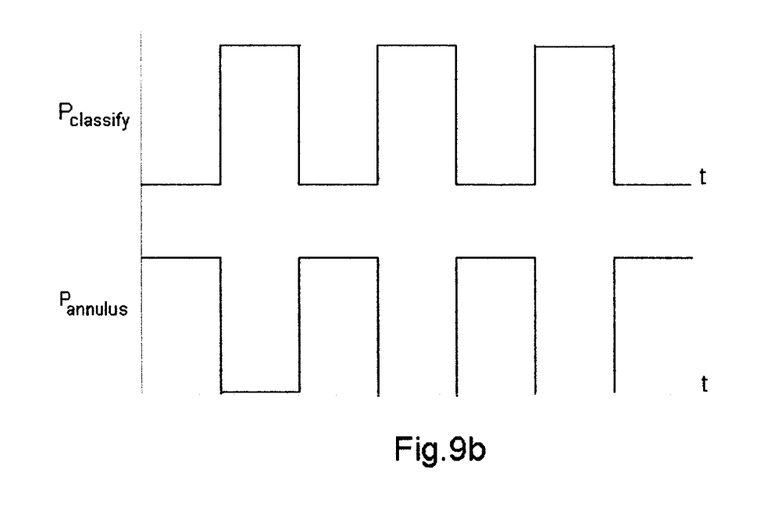
Figure 10:
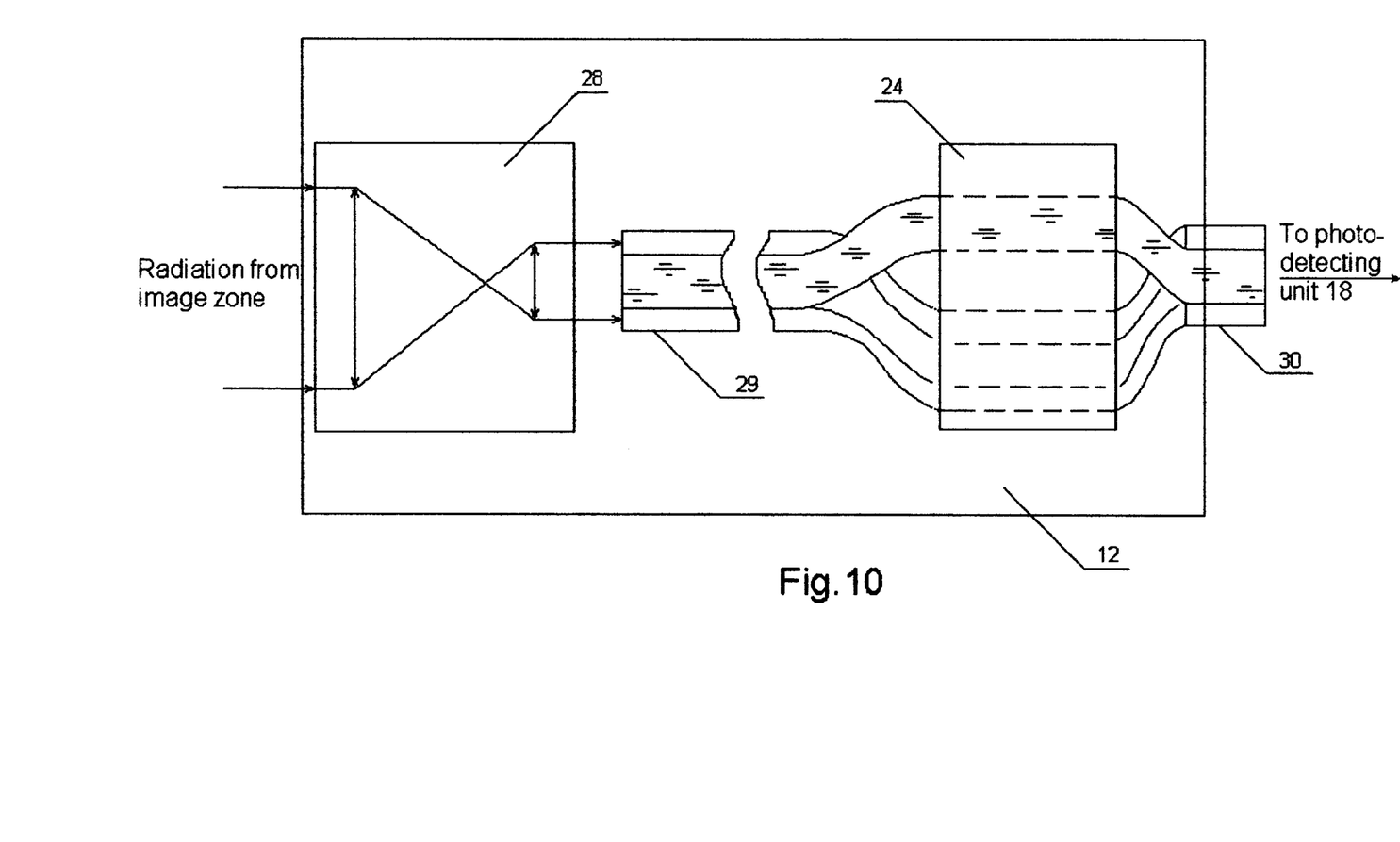
FIG. 10 is an illustration of the image signal forming according to a preferred embodiment

According to another embodiment shown in FIG. 9a the apparatus further comprises an optical alternator 12 arranged for anti-phase amplitude modulation of the radiation of the central area and annulus of the image zone and being placed in the optical way of the image zone radiation in front of the CCD sensor 18. The alternator comprises a spatial beam separator 23 having output optically connected to a spatial light modulator 24. Different types of light modulators as listed in *A new user's guide to spatial light modulators,* by Mark Waring, in "The photonics design and application handbook", A Laurin Publication, pp. 425–428, 1997 can be used. The spatial beam separator 23 separates radiation of the central area and annulus. Spatially separated beams of the radiation are modulated in anti-phase at a frequency of modulation and then are combined in one beam by an optical combiner 25. As it was shown above (equation 11) the A.C. component of the intensity signals at the frequency of modulation is a signal of difference and is used as an image signal with dramatically improved contrast. The optical alternator using a fiber optic splitter 29 and a fiber beam combiner 30 is shown in FIG. 10.

Figure 11:
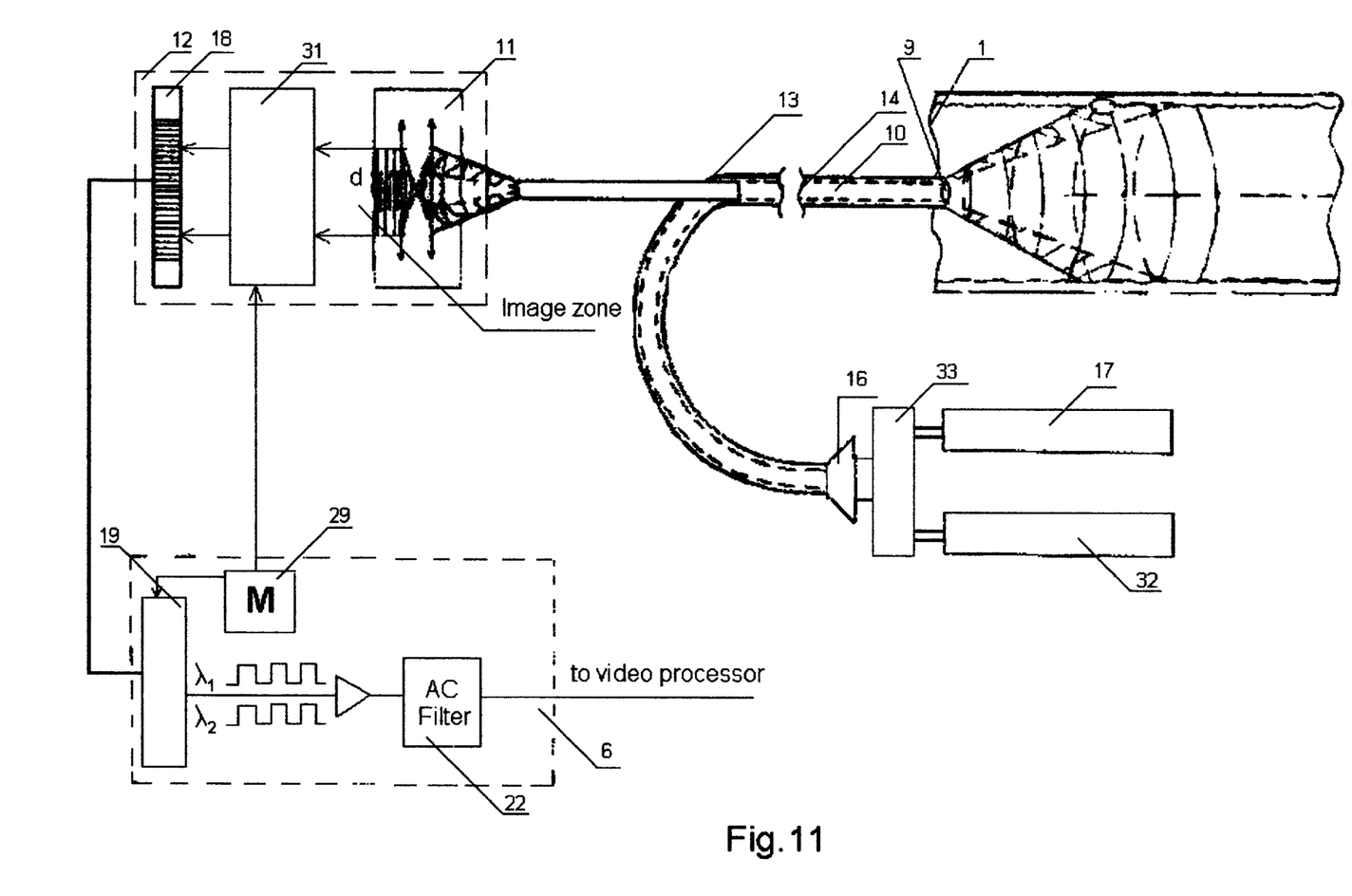
FIG. 11 is a schematic representation of an optical alternator according to a preferred embodiment

Another preferred embodiment of apparatus according to the invention shown in FIG. 11 comprises a source of radiation of a second wavelength 29 having the beam being optically combined with the beam of the source of the first wavelength radiation by an optical beam combiner 33 being optically coupled with the fiber optic coupler 16. The optical beam combiner can be a standard fiber combiner or a known combination of optical elements, such as lenses and mirrors. Thus, dual-wavelength irradiation of the vessel interior is provided and dual-wavelength radiation is reflected and diffused back by the interior. Because the CCD sensor 18 cannot distinguish between different wavelengths of reflected and diffused back radiation a tunable optical filter 31 is arranged in the optical way of diffused back and reflected radiation between the acquiring optics 9 and the CCD 18. Such tunable optical filter is known in pulse oximetry (Design of Pulse Oximeters, edited by J. G. Webster, p. 33, Bristol and Philadelphia, 1997) or a Fabri-Perot interferometer with modulation of the angle of incidence as described in USSR Patent #1,208,475 to Valentin Grimblatov et.al. issued Oct. 1, 1985 can be used. A modulator 32 is arranged in the signal processor 6 for tuning the optical filter and synchronizing the outputs of the read-out circuit 19 with selected by the filter 31 wavelength of radiation being transmitted to the CCD sensor 18. Since the OPL of radiation of the second wavelength in blood is less than the lumen size, the radiation of the second wavelength does not reach the vessel surface and corresponding intensity signals do not contain the contribution of the vessel surface reflection. The outputs of the read-out circuit 19 are also anti-phase modulated. Outside the field of view of the vessel surface the radiation of both wavelengths has substantially the same power and anti-phase modulation does not results in occurrence of the A.C. component. Within the field of view of the surface the intensity signals contain the A.C. component at the frequency of modulation determining by the difference between the intensity signals of the first and second wavelength and being selected by an A.C. filter 22. To adjust the difference in the backscattering of blood at different wavelengths the second wavelength is adjacent to the first wavelength and is selecting from a range 0.8 mkm–1 mkm or from 1.2 mkm to 1.4 mkm.

While the preferred embodiments of the invention illustrate the use of the apparatus for imaging through blood a vessel surface, the invention not limited to such an apparatus. The novel future of the invention can be used for examination of other passages of a human or animal body through physiological fluids.

It will be understood that each of the elements described above, or two or more together, may also find a useful application in other types of methods and constructions differing from the types describe above.

While the invention has been illustrated and described as embodied in method and apparatus for imaging cardiovascular surfaces through blood, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

I claim:

1. A method of imaging a cardiovascular surface through blood comprising the steps of:
    intralumenally irradiating the cardiovascular interior through blood with a radiation of a first wavelength with minimum of total optical losses through blood so that the radiation of the first wavelength is reflected and backscattered at least partly by a cardiovascular surface; detecting all intensity signals of reflected and backscattered radiation; and
    processing the detected intensity signals by selecting the intensity signals of radiation being backscattered by blood only, and subtracting the selected intensity signals of radiation backscattered only by blood from the all detected intensity signals of reflected and backscattered radiation, so as to reconstruct an image of the cardiovascular surface using the intensity signals of difference obtained by said subtracting.

2. A method as defined in claim 1; and further comprising the step of producing an average intensity signal of the radiation being backscattered only by blood and subtracting the average intensity signal from the all detected intensity signals of reflected and backscattered radiation.

3. A method as defined in claim 1; wherein said selecting includes forming an image zone radiation.

4. A method as defined in claim 1; wherein said selecting includes locating an area of the image zone corresponding to radiation backscattered only by blood.

5. A method as defined in claim 4; wherein said locating includes using a central area of the image zone confined by a circumference determining from expression $$d_0 = \frac{\left(2f\sqrt{l_{max}^2 - \frac{D^2}{4}}\right)}{l_{max}}$$

where D is a diameter of the cardiovascular passage, $l_{max}$ is a maximal optical path length in blood and f is a focal length of the image zone forming optics.

6. A method as defined in claim 1, wherein said processing includes anti-phase amplitude modulating the intensity signals of radiation of the located area and annulus at a frequency of modulation and filtering an A.C. component of the intensity signals at the frequency of modulation.

7. A method as defined in claim 1, wherein said irradiating with the radiation of a first wavelength includes using the first wavelength of substantially 1 mkm–1.2 mkm.

8. A method as defined in claim 1, and further comprising the step of intralumenally irradiating the cardiovascular interior with radiation of a second wavelength corresponding to an optical path length in blood being less than a cardiovascular lumen size, and optical selecting the first and the second wavelength components of the reflected and backscattered radiation.

9. A method as defined in claim 8, wherein said optical selecting includes alternative optical filtrating the components of the first and the second wavelength of radiation reflected and backscattered from the cardiovascular interior at a frequency of alternation, said processing includes electronic filtrating the A.C. component of the intensity signals at the frequency of alternation.

10. A method as defined in claim 8, wherein said intralumenally irradiating includes irradiating within a ring shaped cone.

11. A method as defined in claim 8, wherein said intralumenally irradiating with the radiation of a second wavelength includes using the second wavelength of substantially 0.8 mkm–1 mkm.

12. A method as defined in claim 8, wherein said intralumenally irradiating with the radiation of a second wavelength includes using the second wavelength of substantially 1.2 mkm–1.4 mkm.

13. An apparatus for imaging a cardiovascular surface through blood, comprising:
    means for intraluminally irradiating a cardiovascular interior through blood with a radiation of a first wavelength with minimum of total optical losses through blood so that the radiation of a first wavelength is reflected and backscattered at least partly from a cardiovascular surface;
    means for detecting all intensity signals of reflected and backscattered radiation; and
    means for processing the detected intensity signals by selecting the intensity signals of radiation backscattered by blood only, and subtracting the selected intensity signals of radiation backscattered only by blood from the all detected intensity signals of reflected and backscattered radiation, so as to reconstruct an image of the cardiovascular surface using the intensity signals of difference obtained by said subtracting.

14. An apparatus as defined in claim 13, wherein said for intralumenally irradiating and detecting means include a scope with distal and proximal ends having a transmission channel for transmitting the radiation from a source of a first wavelength into the lumen of a blood vessel, and an acquisition channel for detecting reflected and backscattered from the vessel interior radiation with an acquiring optics for collecting and transforming the reflected and backscattered radiation into radiation of an image zone being engaged with the distal end of the scope and a photodetector for detecting the radiation of the image zone being optically connected to the acquiring optics.

15. An apparatus as defined in claim 14, wherein said source of radiation of the first wavelength is engaged with a fiber coupler, which is optically connected to the proximal end of the transmission channel.

16. An apparatus as defined in claim 15, wherein the source of radiation is a laser.

17. An apparatus as defined in claim 15, wherein the source of radiation is a Light Emitted Diode.

18. An apparatus as defined in claim 14, wherein said acquisition channel includes a fiber optic cable for transmitting a collected radiation to said proximal end of said scope and engaged with said acquiring optics, and an image optic for forming the image zone of radiation that is engaged with the proximal end of the scope and optically connected to said photodetector.

19. An apparatus as defined in claim 18, wherein said acquisition channel further includes an optical alternator arranged for anti-phase amplitude modulation of the radiation of a central area and annulus being placed in an optical way between said photodetector and said image optics and said signal processor is an A.C. electronic filter.

20. An apparatus as defined in claim 19, wherein said optical alternator includes a spatial beam separator arranged for spatial separation of radiation of a classified area and annulus being optically connected to said image optics and an optical modulator arranged for anti-phase amplitude modulation of spatially separated beams having input optically connected to a spatial beam separator and output being optically connected to an optical beam combiner arranged for combining modulated beams and said signal processor further including a controller for driving said spatial optical modulator.

21. An apparatus as defined in claim 20, wherein said spatial beam separator and said optical beam combiner are a fiber optic splitter and a fiber optic combiner accordingly.

22. An apparatus as defined in claim 20, further comprising a source of radiation of a second wavelength optically connected to an optical beam combiner arranged for combining radiation of the first and second wavelength and a tunable optical filter for alternative optical selection of the first and second wavelength components of radiation being reflected by and diffused back from the vessel interior engaged with said photodetector and said signal processor including a modulator for synchronization read-out-circuit outputs with a wavelength selection being electrically connected to a tunable optical filter and read-out-circuit and an A.C. filter for filtering out an A.C. component of the intensity signals at a frequency of alternative optical selection.

23. An apparatus as defined in claim 13, wherein said processing means include a signal processor for producing image signals comprising a read-out-circuit arranged for selecting outputs accordingly to predetermined settings and being electrically connected to a first and a second amplifier, and a signal subtractor arranged for producing image signals of difference and electrically connected to said first and said second amplifier.

24. An apparatus as defined in claim 23, wherein said signal processor includes a signal averaging unit for producing an average intensity signal of radiation backscattered only by blood, said signal subtractor producing image signals of difference and being electrically connected to said first amplifier and said signal averaging unit.

25. An apparatus as defined in claim 24, wherein said signal subtractor includes a modulator for anti-phase amplitude modulating the intensity signals at a frequency of modulation and is electrically connected to said signal average unit, said first amplifier and an A.C. electronic filter for filtering an A.C. component of the intensity signals and a frequency of modulation being electrically connected to said modulator.

* * * * *